US007838825B2

(12) United States Patent
Vakhshoori et al.

(10) Patent No.: US 7,838,825 B2
(45) Date of Patent: Nov. 23, 2010

(54) METHOD AND APPARATUS FOR INCORPORATING ELECTROSTATIC CONCENTRATORS AND/OR ION MOBILITY SEPARATORS WITH RAMAN, IR, UV, XRF, LIF AND LIBS SPECTROSCOPY AND/OR OTHER SPECTROSCOPIC TECHNIQUES

(75) Inventors: Daryoosh Vakhshoori, Cambridge, MA (US); Peili Chen, Andover, MA (US)

(73) Assignee: Ahura Scientific Inc., Wilmington, MA (US)

( * ) Notice: Subject to any disclaimer, the term of this patent is extended or adjusted under 35 U.S.C. 154(b) by 729 days.

(21) Appl. No.: 11/706,043

(22) Filed: Feb. 13, 2007

(65) Prior Publication Data

US 2009/0014646 A1 Jan. 15, 2009

Related U.S. Application Data

(60) Provisional application No. 60/772,662, filed on Feb. 13, 2006.

(51) Int. Cl.
*H01J 49/40* (2006.01)

(52) U.S. Cl. ....................... 250/288; 250/281; 250/292; 356/301; 356/318; 356/328; 702/76

(58) Field of Classification Search ....................... None
See application file for complete search history.

(56) References Cited

U.S. PATENT DOCUMENTS 5,646,729 A 7/1997 Koskinen et al.
5,914,454 A 6/1999 Imbaro et al.
6,635,105 B2 10/2003 Ahlborn et al.
6,919,959 B2 7/2005 Masten
7,012,249 B2 * 3/2006 Krutchinsky et al. ........ 250/288
7,047,810 B2 5/2006 Kogan et al.
7,057,791 B2 6/2006 Azimi et al.
7,062,133 B2 6/2006 Azimi et al.
7,068,905 B2 6/2006 Vakhshoori et al.
7,099,004 B2 8/2006 Masten
7,110,109 B2 9/2006 Knopp et al.
7,113,814 B2 9/2006 Ward et al.
D534,446 S 1/2007 Knopp et al.
7,164,121 B2 1/2007 Hirano et al.
7,180,653 B2 2/2007 Knopp et al.
7,190,861 B2 3/2007 Knopp et al.
7,215,836 B2 5/2007 Vakhshoori et al.
7,254,501 B1 8/2007 Brown et al.
7,289,208 B2 10/2007 Vakhshoori et al.
7,302,136 B2 11/2007 Vakhshoori et al.
7,344,905 B2 3/2008 Wang et al.
7,362,423 B2 4/2008 Masten
7,409,125 B2 8/2008 Azimi et al.
7,417,731 B1 8/2008 Masten
7,420,672 B2 9/2008 Wang et al.
7,499,159 B2 3/2009 Knopp et al.
2004/0079876 A1 4/2004 Hirano et al.
2005/0225758 A1 10/2005 Knopp et al.
2005/0248759 A1 11/2005 Wang et al.
2006/0045151 A1 3/2006 Vakhshoori et al.

(Continued)

*Primary Examiner*—David A Vanore
(74) *Attorney, Agent, or Firm*—Fish & Richardson P.C.

(57) ABSTRACT

The present invention provides a novel approach for reliably and accurately detecting and identifying airborne particles. This is done by providing a novel system which incorporates electrostatic concentrators and/or ion mobility separators with Raman, IR, UV, XRF, LIF and LIBS spectroscopy and/or other spectroscopic techniques.

21 Claims, 6 Drawing Sheets

U.S. PATENT DOCUMENTS

| | | | |
|---|---|---|---|
| 2006/0088069 | A1 | 4/2006 | Vakhshoori et al. |
| 2006/0170917 | A1 | 8/2006 | Vakhshoori et al. |
| 2007/0002319 | A1 | 1/2007 | Knopp et al. |
| 2007/0058243 | A1 | 3/2007 | Vakhshoori et al. |
| 2007/0074574 | A1 | 4/2007 | Kogan et al. |
| 2007/0091412 | A1 | 4/2007 | Azimi et al. |
| 2007/0116069 | A1 | 5/2007 | Wang et al. |
| 2008/0033663 | A1 | 2/2008 | Brown et al. |
| 2008/0060455 | A1 | 3/2008 | Coyle |
| 2008/0069169 | A1 | 3/2008 | Wang et al. |
| 2008/0170223 | A1 | 7/2008 | Vakhshoori et al. |
| 2008/0291426 | A1 | 11/2008 | Azimi et al. |
| 2009/0010597 | A1 | 1/2009 | Azimi et al. |
| 2009/0014646 | A1 | 1/2009 | Vakhshoori et al. |
| 2009/0033928 | A1 | 2/2009 | Azimi et al. |

* cited by examiner

METHOD AND APPARATUS FOR INCORPORATING ELECTROSTATIC CONCENTRATORS AND/OR ION MOBILITY SEPARATORS WITH RAMAN, IR, UV, XRF, LIF AND LIBS SPECTROSCOPY AND/OR OTHER SPECTROSCOPIC TECHNIQUES

REFERENCE TO PENDING PRIOR PATENT APPLICATION

This patent application claims benefit of pending prior U.S. Provisional Patent Application Ser. No. 60/772,662, filed Feb. 13, 2006 by Daryoosh Vakhshoori et al. for METHOD OF INCORPORATING ELECTROSTATIC CONCENTRATOR OR ION MOBILITY SEPARATOR WITH RAMAN, INFRARED, UV, XRF, LIBS, OR SIMILAR SPECTROSCOPIC TECHNIQUES, which patent application is hereby incorporated herein by reference.

FIELD OF THE INVENTION

This patent application relates to methods and apparatus for the detection and identification of airborne particles in general, and more particularly to a method and apparatus for incorporating electrostatic concentrators and/or ion mobility separators with Raman spectroscopy, infrared (IR) spectroscopy, ultra-violet (UV) spectroscopy, X-ray fluorescence (XRF) spectroscopy, laser-induced fluorescence (LIF) spectroscopy and laser-induced breakdown (LIBS) spectroscopy and/or other spectroscopic techniques.

As used herein, the term “particle” is meant to include aggregates of various sizes, including structures comprising a single molecule.

BACKGROUND OF THE INVENTION

Airborne particles can be significant sources of industrial hazards (e.g., pollutants), health hazards (e.g., biomolecules) and/or public security threats (e.g., chemical and/or biological agents). For this reason, it is desirable to have systems capable of detecting and identifying such particles. The market for such systems is sizable and can extend well beyond government and industrial health and security applications, e.g., the market can extend to air quality monitoring for buildings, inventory inspections, food and drug qualification and authentication applications, etc.

Unfortunately, current systems for detecting and identifying such particles generally rely on gas sensors and are not sufficiently reliable and/or accurate. This is especially true for low vapor pressure particulates, since traditional gas sensors (which are primarily sensitive to gaseous molecules) are generally ineffective for such particulates.

Raman or Fourier transform IR (FTIR) absorption spectroscopy is known to be selective and accurate when it comes to detecting and identifying solids and liquids. However, these analysis techniques generally require a minimum mass of material to analyze. This can be difficult to achieve with airborne particles, and particularly low vapor pressure particulates. Hence, Raman and FTIR spectroscopy has not heretofore been used extensively for detecting and identifying airborne particles.

One possible solution would be to combine a particle concentrator and/or a particle separator with a Raman or FTIR spectroscopic analyzer. However, traditional concentrator geometries (such as conventional electrostatic concentrators or liquid concentrators) generally do not produce a high enough concentration on a surface to be compatible with Raman or FTIR spectroscopy. Furthermore, where the specimen contains multiple particulate species, concentrating enough of the particulates on a surface so as to enable Raman or FTIR spectroscopy can present a new problem, namely, there may be too many different types of airborne species on the analyzer surface, lumped one on top of another. Such lumping of multiple particulate species can make isolation of the individual spectral signatures (and hence identification of the component particulate species) quite difficult.

SUMMARY OF THE INVENTION

The present invention provides a novel approach for reliably and accurately detecting and identifying airborne particles. This is done by providing a novel system which incorporates electrostatic concentrators and/or ion mobility separators with Raman, IR, UV, XRF, LIF and LIBS spectroscopy and/or other spectroscopic techniques.

The present invention also provides a novel approach for locally increasing the concentration of airborne particles using a unique electrostatic concentrator geometry, whereby to enable the use of spectroscopic techniques to identify the particles.

The present invention also provides a novel approach to first separate, and then concentrate, different species of airborne particles so as to enable the use of spectroscopic techniques to locally identify the separated species of particles. More particularly, the present invention provides a novel approach for using ion mobility separators to separate different species of airborne particles from one another, and then using electrostatic concentrators to concentrate the different species of airborne particles at different locations on an analyzer surface, whereby to enable the use of spectroscopic techniques to identify each of species of the particles.

In one form of the present invention, there is provided apparatus for reliably and accurately detecting and identifying airborne particles, comprising:

an electrostatic concentrator for concentrating airborne particles about a site; and a spectrometer for identifying the airborne particles concentrated about the site.

In another form of the present invention, there is provided apparatus for reliably and accurately detecting and identifying airborne particles, comprising:

an ion mobility separator for separating different species of airborne particles from one another;

at least one electrostatic concentrator for concentrating the separated different species of airborne particles about at least one site; and at least one spectrometer for identifying the airborne particles concentrated about the at least one site.

In another form of the present invention, there is provided a method for reliably and accurately detecting and identifying airborne particles, comprising:

providing apparatus comprising:

an electrostatic concentrator for concentrating airborne particles about a site; and a spectrometer for identifying the airborne particles concentrated about the site;

passing the airborne particles across the electrostatic concentrator while operating the electrostatic concentrator so as to concentrate the airborne particles about the site; and operating the spectrometer so as to identify the airborne particles concentrated about the site.

In another form of the present invention, there is provided a method for reliably and accurately detecting and identifying airborne particles, comprising:

providing apparatus comprising:

an ion mobility separator for separating different species of airborne particles from one another;

at least one electrostatic concentrator for concentrating the separated different species of airborne particles about the at least one site; and at least one spectrometer for identifying the airborne particles concentrated about the at least one site;

passing the airborne particles across the ion mobility separator while operating the ion mobility separator so as to separating different species of airborne particles from one another;

passing the airborne particles across the at least one electrostatic concentrator while operating the electrostatic concentrator so as to concentrate the separated different species of airborne particles about the at least one site; and operating the at least one spectrometer so as to identify the airborne particles concentrated about the at least one site.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein.

DETAILED DESCRIPTION OF THE PRESENT INVENTION

The present invention provides a novel approach for reliably and accurately detecting and identifying airborne particles. This is done by providing a novel system which incorporates electrostatic concentrators and/or ion mobility separators with Raman, IR, UV, XRF, LIF and LIBS spectroscopy and/or other spectroscopic techniques.

Electrostatic Concentrator with Spectroscopic Analysis

The present invention provides a novel approach for locally increasing the concentration of airborne particles using a unique electrostatic concentrator geometry, whereby to enable the use of spectroscopic techniques to identify the particles.

In traditional Raman spectrometry, which is typically directed to the identification of solids and liquids, a small spot mass of specimen material is adequate to perform Raman spectral collection and hence identification of the specimen. Raman analyzers utilizing multimode lasers as the pump laser can have a spot size on the order of ~100 mm, whereas Raman analyzers utilizing a single mode laser can process sampling spots down to ~10 mm.

Airborne particles are generally considered to have diameters in the range of a few hundred nanometers to a few microns. Therefore, because of low Raman cross-section scattering, it is not possible to utilize conventional Raman analyzers, which have a relatively large spot size of ~100 mm in the case of multimode pump lasers and a relatively large spot size of ~10 mm in the case of single mode pump lasers.

Therefore, in accordance with the present invention, it is important to focus the Raman pump laser on the area filled with the collected airborne particles. More particularly, in the novel geometry of the present invention, an electrostatic concentrator is provided to attract the airborne particles specifically to the small area where the Raman pump laser is focused.

Figure 1:
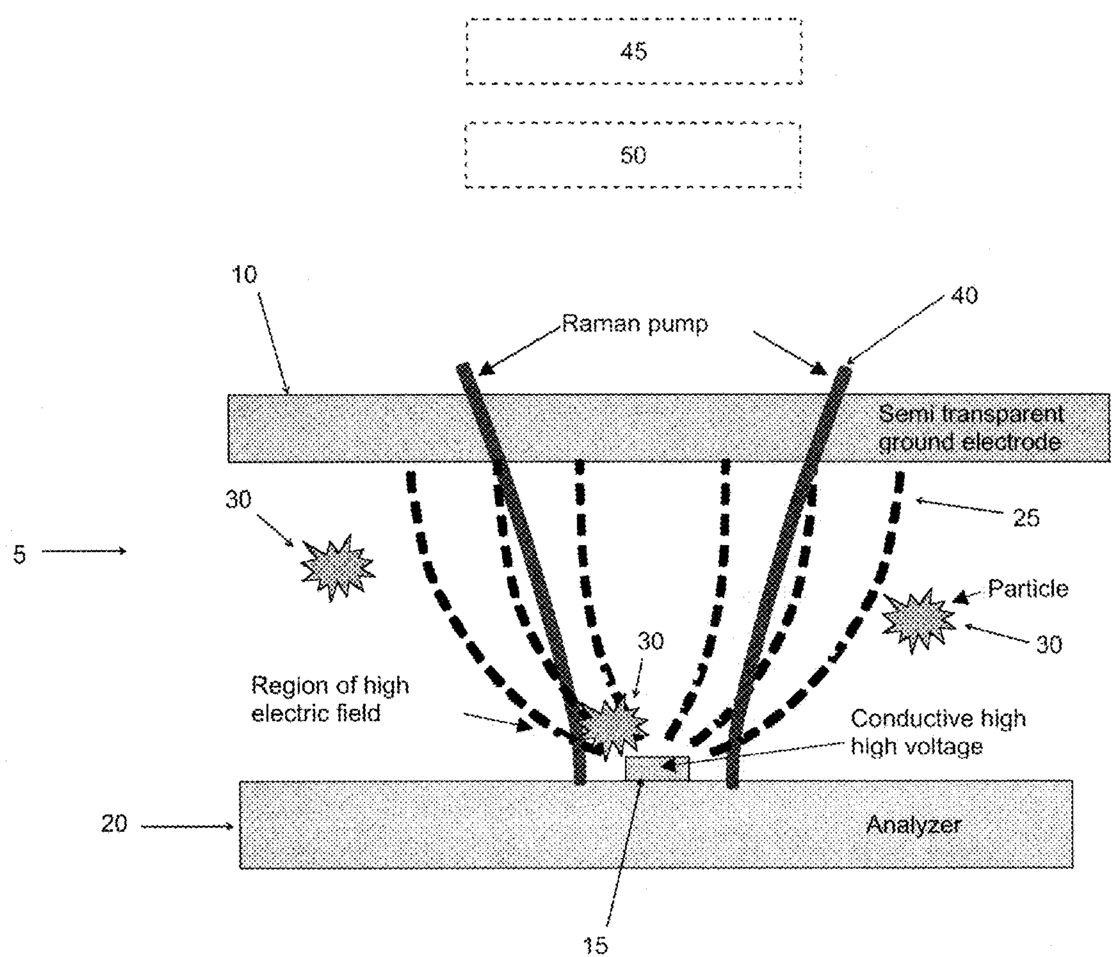
FIG. 1 is a schematic diagram showing a first approach for using an electrostatic concentrator to locally increase the concentration of airborne particles so as to facilitate spectroscopic identification, with the source light (e.g., the Raman pump light) passing through a top semi-transparent ground electrode and being focused on or near the bottom high voltage (i.e., collection) electrode.

More particularly, and looking now at FIG. 1, there is shown an electrostatic concentrator 5 which comprises a semi-transparent ground electrode 10 and a conductive high voltage electrode 15 mounted to an analyzer 20. The electrode geometry is constructed so as to generate an electrical field 25 having a large gradient in a small area, and since the force on neutral airborne particles 30 is proportional to the gradient of the electric field, these airborne particles 30 are guided toward the highest gradient, which is designed to be on the surface of analyzer 20. In this way, a sufficient quantity of airborne particles 30 can be gathered so as to provide a specimen size which is amenable to Raman spectroscopy.

At the same time, the light 40 from a Raman pump laser 45 is focused by one or more lenses 50 through the semi-transparent ground electrode 10 and onto the region of conductive high voltage electrode 15, i.e., onto the aggregated mass of airborne particles 30 concentrated about high voltage electrode 15. The incidence of pump light 40 on the aggregated airborne particles 30 results in the generation of a Raman signature, which is then read by analyzer 20 and used to identify the composition of airborne particles 30.

In the foregoing description of the construction shown in FIG. 1, Raman spectroscopy is the spectroscopic technique used to analyze the composition of the airborne particles 30 aggregated by the electrostatic concentrator 5. However, it should also be appreciated that other spectroscopic techniques may also be used to identify the composition of the airborne particles aggregated by the electrostatic concentrator 5, e.g., IR spectroscopy, UV spectroscopy, XRF spectroscopy, LIF spectroscopy and LIBS spectroscopy and/or other spectroscopic techniques. Thus, for example, one can perform UV or XRF spectroscopy if the Raman pump laser is replaced by a UV or X-ray source. Also, LIBS can be used by focusing a high peak power laser onto the particle, thereby generating a plasma and detecting the corresponding optical emission spectrum.

Other constructions may also be used without departing from the scope of the present invention.

Figure 2:
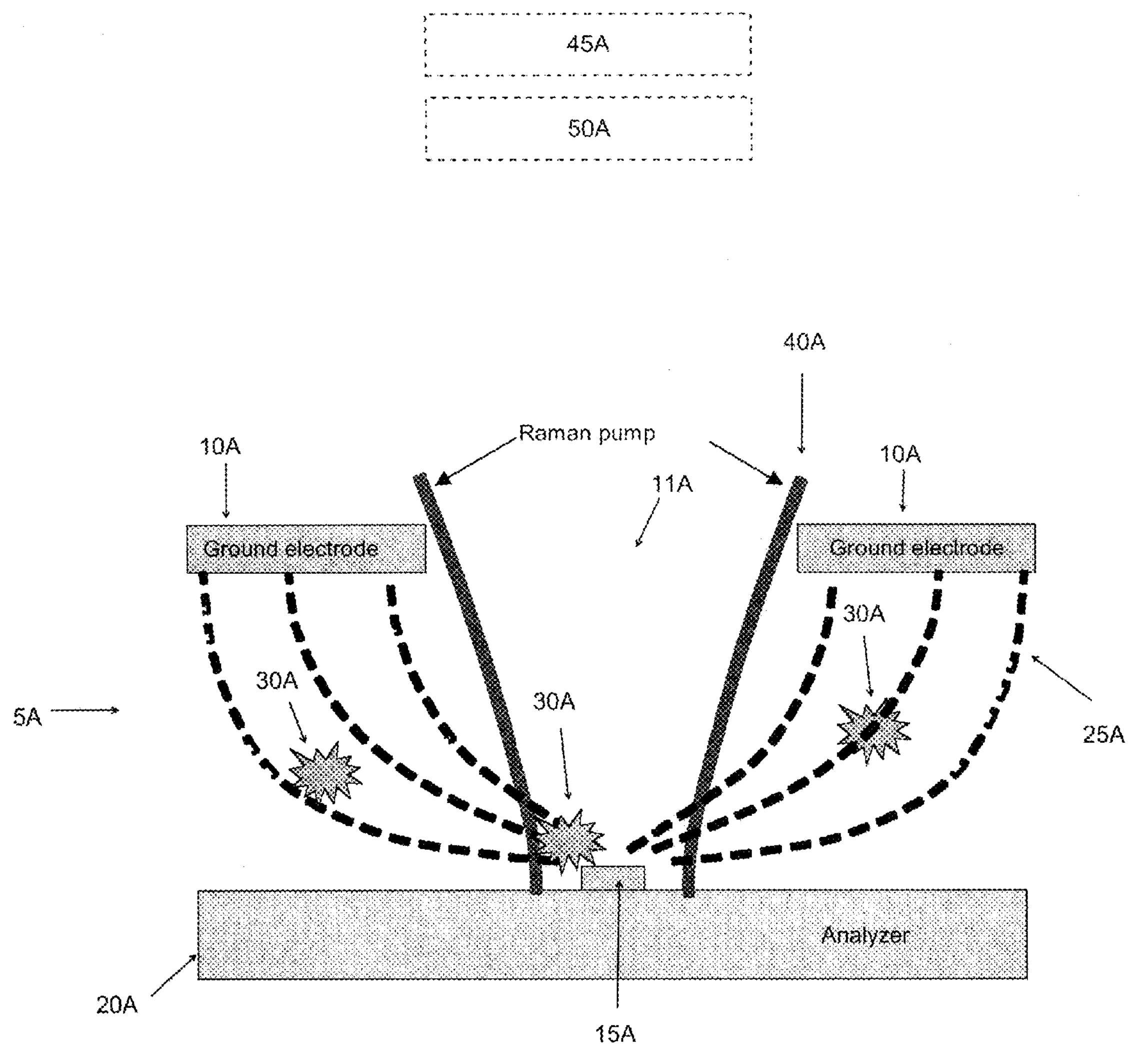
FIG. 2 is a schematic diagram showing a second approach for using an electrostatic concentrator to locally increase the concentration of airborne particles so as to facilitate spectroscopic identification, with the source light passing through a hole in the top ground electrode and being focused on or near the bottom high voltage (i.e., collection) electrode.

Thus, for example, and looking now at FIG. 2, there is shown an electrostatic concentrator 5A which comprises a ground electrode 10A having an opening 11A formed therein and a conductive high voltage electrode 15A mounted to an analyzer 20A. The electrode geometry is constructed so as to generate an electrical field 25A having a large gradient in a small area, and since the force on neutral airborne particles 30A is proportional to the gradient of the electric field, these airborne particles 30A are guided toward the highest gradient, which is designed to be on the surface of analyzer 20A. In this way, a sufficient quantity of airborne particles 30A can be gathered so as to provide a specimen size which is amenable to Raman spectroscopy.

At the same time, the light 40A from a Raman pump laser 45A is focused by one or more lenses 50A through the opening 11A formed in ground electrode 10A and onto the region of conductive high voltage electrode 15A, i.e., onto the aggregated mass of airborne particles 30A concentrated about high voltage electrode 15A. The incidence of pump light 40A on the aggregated airborne particles 30A results in the generation of a Raman signature, which is then read by analyzer 20A and used to identify the composition of airborne particles 30A.

In the foregoing description of the construction shown in FIG. 2, Raman spectroscopy is the spectroscopic technique used to analyze the composition of the airborne particles 30A aggregated by the electrostatic concentrator 5A. However, it should also be appreciated that other spectroscopic techniques may also be used to identify the composition of the airborne particles aggregated by the electrostatic concentrator 5A, e.g., IR spectroscopy, UV spectroscopy, XRF spectroscopy, LIF spectroscopy and LIBS spectroscopy and/or other spectroscopic techniques. Thus, for example, one can perform UV or XRF spectroscopy if the Raman pump laser is replaced by a UV or X-ray source. Also, LIBS can be used by focusing a high peak power laser onto the particle, thereby generating a plasma and detecting the corresponding optical emission spectrum.

Figure 3:
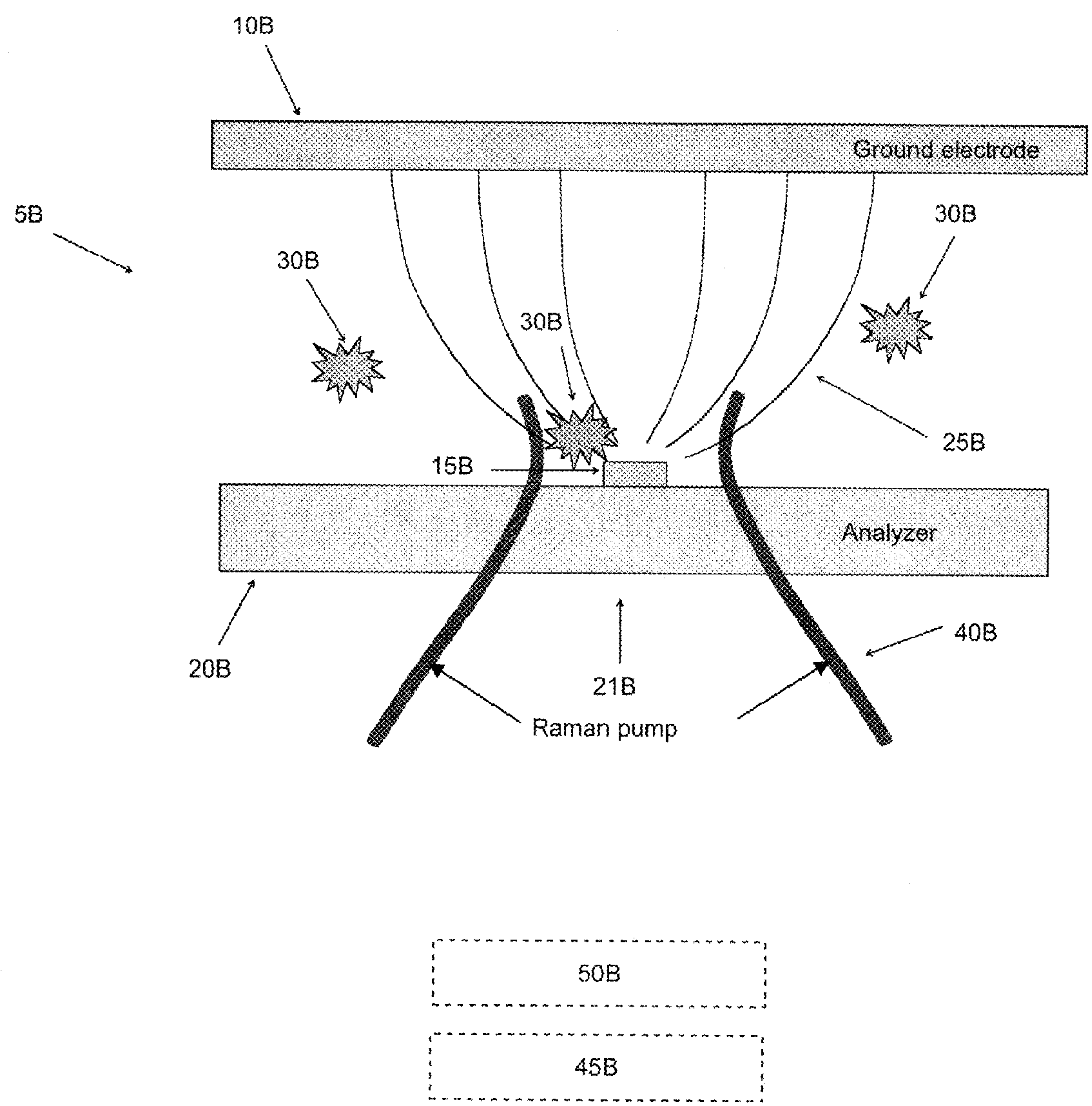
FIG. 3 is a schematic diagram showing a third approach for using an electrostatic concentrator to locally increase the concentration of airborne particles so as to facilitate spectroscopic identification, with the source light passing through the bottom high voltage (i.e., collection) electrode.

Furthermore, and looking now at FIG. 3, there is shown an electrostatic concentrator 5B which comprises a ground electrode 10B and a conductive high voltage electrode 15B mounted to an analyzer 20B having a transparent region 21B adjacent to conductive high voltage electrode 15B. The electrode geometry is constructed so as to generate an electrical field 25B having a large gradient in a small area, and since the force on neutral airborne particles 30B is proportional to the gradient of the electric field, these airborne particles 30B are guided toward the highest gradient, which is designed to be on the surface of analyzer 20B. In this way, a sufficient quantity of airborne particles 30B can be gathered so as to provide a specimen size which is amenable to Raman spectroscopy.

At the same time, the light 40B from a Raman pump laser 45B is focused by one or more lenses 50B through the transparent region 21B of analyzer 20B and onto the region of conductive high voltage electrode 15B, i.e., onto the aggregated mass of airborne particles 30B concentrated about high voltage electrode 15B. In this case, it may also be convenient and/or desirable to form conductive high voltage electrode 15B out of a semi-transparent material. The incidence of pump light 40B on the aggregated airborne particles 30B results in the generation of a Raman signature, which is then read by analyzer 20B and used to identify the composition of airborne particles 30B.

In the foregoing description of the construction shown in FIG. 3, Raman spectroscopy is the spectroscopic technique used to analyze the composition of the airborne particles 30B aggregated by the electrostatic concentrator 5B. However, it should also be appreciated that other spectroscopic techniques may also be used to identify the composition of the airborne particles aggregated by the electrostatic concentrator 5B, e.g., IR spectroscopy, UV spectroscopy, XRF spectroscopy, LIF spectroscopy and LIBS spectroscopy and/or other spectroscopic techniques. Thus, for example, one can perform UV or XRF spectroscopy if the Raman pump laser is replaced by a UV or X-ray source. Also, LIBS can be used by focusing a high peak power laser onto the particle, thereby generating a plasma and detecting the corresponding optical emission spectrum.

In addition to the foregoing, if the geometry shown in FIG. 3 is used, it may be preferable to use a low Raman cross-section material (such as glass or a substrate with few and well-defined Raman peaks) for the transparent region 21B of analyzer 20B.

Ion Mobility Separator and Electrostatic Concentrator with Spectroscopic Analysis The present invention also provides a novel approach to first separate, and then concentrate, different species of airborne particles so as to enable the use of spectroscopic techniques to locally identify the separated species of particles. More particularly, the present invention provides a novel approach for using ion mobility separators to first separate different species of airborne particles from one another, and then using electrostatic concentrators to thereafter concentrate the different species of airborne particles at different locations on an analyzer surface, whereby to enable the use of spectroscopic techniques to identify each of the species of the airborne particles.

Figure 4:
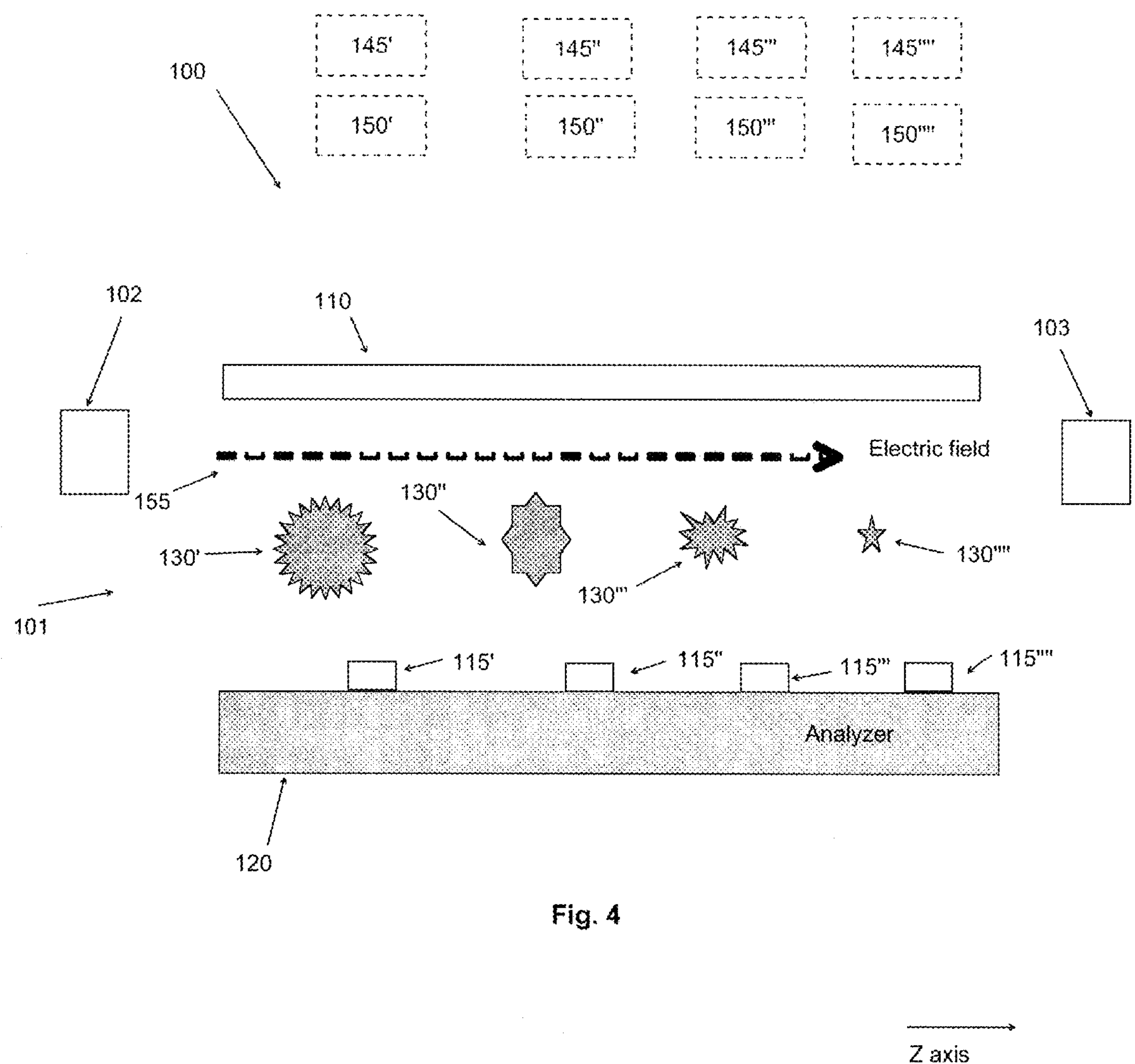
FIG. 4 is a schematic diagram showing how an ion mobility separator can be used to separate different airborne particles at different locations along an analyzer.
Figure 5:
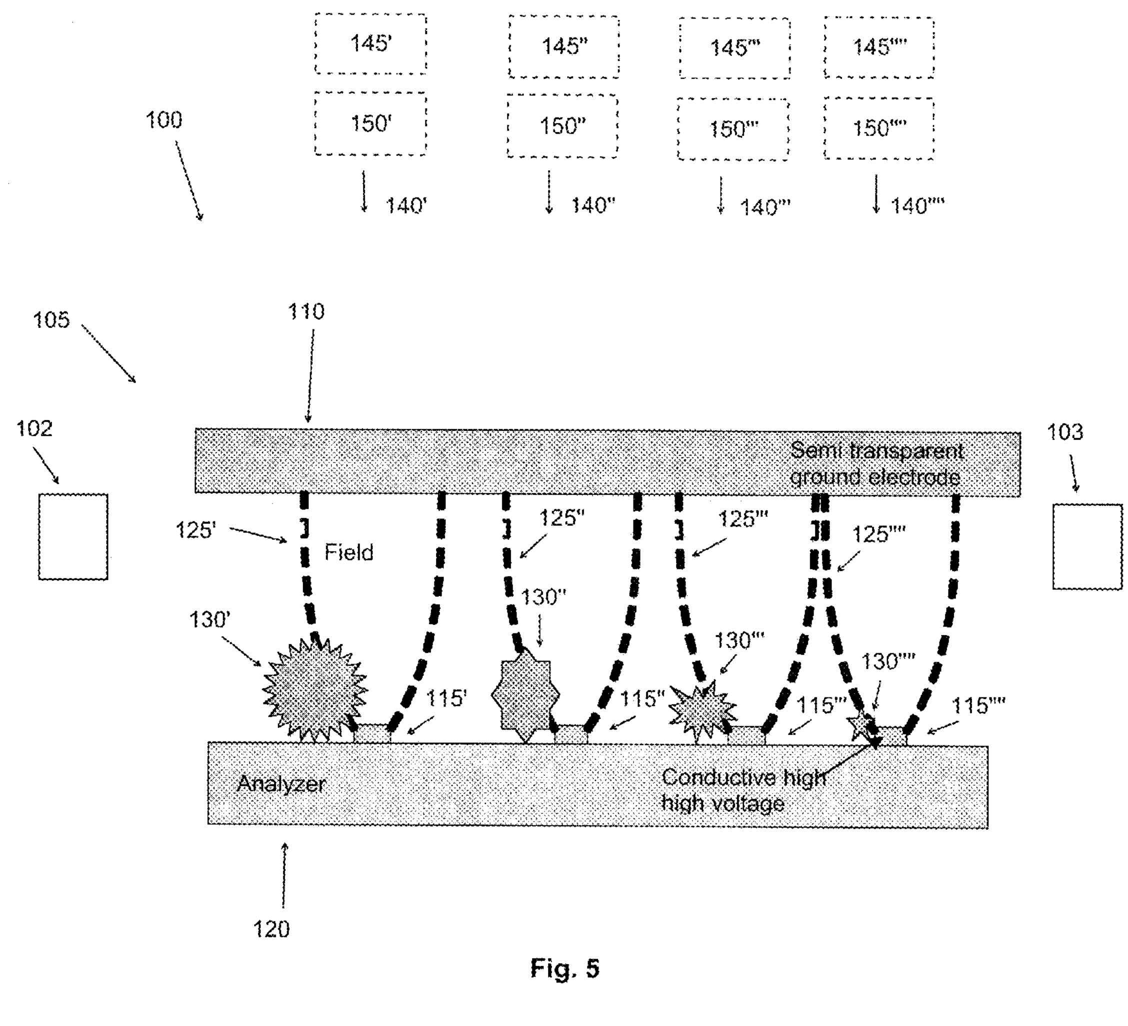
FIG. 5 is a schematic diagram showing how an ion mobility separator is used in conjunction with an electrostatic concentrator to first separate, and then concentrate, different species of airborne particles.

Thus, and looking now at FIGS. 4 and 5, there is shown a device 100 comprising an ion mobility separator 101 which can be used to first separate different species of airborne particles from one another using differences in ion mobility, and an electrostatic concentrator assembly 105 which can thereafter be used to concentrate the separated species of airborne particles at different locations along the analyzer using a plurality of electrostatic concentrators, whereby to facilitate identification using spectroscopic techniques.

More particularly, and looking now at FIG. 4, ion mobility separator 101 comprises a pair of electrodes 102, 103 which create an electric field E(z) 155 which extends along the Z axis of analyzer 120. As a result of this construction, when airborne particles 130 (comprising a plurality of different species 130', 130'', 130''' and 130'''') are ionized using techniques well known in the field of ion mobility separation, and then those airborne particles 130', 130'', 130''' and 130'''' are allowed to drift within electric field E(z) 155, the different ion mobilities of the species in air or other gases will cause airborne particles 130', 130'', 130''' and 130'''' to migrate to different positions along the Z axis of analyzer 120 for any given duration of the application of the E(z) electric field 155. Thus, ion mobility separator 101 can be used to separate the different species of airborne particles from one another.

Looking now at FIG. 5, device 100 also comprises electrostatic concentrator assembly 105. Electrostatic concentrator assembly 105 preferably comprises a semi-transparent ground electrode 110 and a plurality of conductive high voltage electrodes 115', 115'', 115''', 115'''' mounted to analyzer 120. The electrode geometry is constructed so as to generate a plurality of electrical fields 125', 125'', 125''', 125'''' having a large gradient in a small area, and since the force on airborne particles 130 is proportional to the gradient of the electric field, these airborne particles 130 are guided toward the highest gradient, which is designed to be on the surface of analyzer 120. In this way, sufficient quantities of airborne particles 130 can be gathered so as to provide a specimen size which is amenable to Raman spectroscopy.

Thus, if ion mobility separator 101 is first used to separate the various species 130', 130", 130'", 130"" along the Z axis of analyzer 120 using the electric field E(z) 155, and then the electric field E(z) 155 is reduced to zero, and if additional electric fields E(x) 125', 125", 125'", 125"" are then established along the X axis, these additional electric fields E(x) 125', 125", 125'", 125"" will pull the particles 130', 130", 130'", 130"" down to the conductive high voltage electrodes 115', 115", 115'", 115"" on the analyzer 120 and immobilize the particles there. In this way, the ion mobility separator 101 may first be used to separate the various species 130', 130", 130'", 130"" at different locations along the analyzer 120, and then the plurality of conductive high voltage electrodes 115', 115", 115'", 115"" may be used to concentrate the various species 130', 130", 130'", 130"" about the various electrodes 115', 115", 115'", 115"".

At this point, light 140', 140", 140'", 140"" from Raman pump lasers 145', 145", 145'", 145"" is focused by a plurality of lenses 150', 150", 150", 150"" through the semi-transparent ground electrode 110 and onto the regions of conductive high voltage electrode 115', 115", 115'", 115"", i.e., onto the aggregated mass of airborne particles 130', 130", 130'", 130"" concentrated, respectively, about high voltage electrodes 115', 115", 115'", 115"". The incidence of pump light 140', 140", 140'", 140"" onto the aggregated airborne particles 130', 130", 130'", 130"" results in the generation of Raman signatures, which are then read by analyzer 120 and used to identify the composition of airborne particles 130', 130", 130'", 130"".

In the foregoing description of the construction shown in FIGS. 4 and 5, Raman spectroscopy is the spectroscopic technique used to analyze the composition of the airborne particles 130 aggregated by the electrostatic concentrator assembly 105. However, it should also be appreciated that other spectroscopic techniques may also be used to identify the composition of the airborne particles aggregated by the electrostatic concentrator 105, e.g., IR spectroscopy, UV spectroscopy, XRF spectroscopy, LIF spectroscopy and LIBS spectroscopy and/or other spectroscopic techniques. Thus, for example, one can perform UV or XRF spectroscopy if the Raman pump laser is replaced by a UV or X-ray source. Also, LIBS can be used by focusing a high peak power laser onto the particle, thereby generating a plasma and detecting the corresponding optical emission spectrum.

Other constructions may also be used without departing from the scope of the present invention.

Thus, for example, the electrostatic concentrator assembly 105 can use a construction analogous to that shown in FIG. 2 or a construction analogous to that shown in FIG. 3, rather than using a construction analogous to that shown in FIG. 1.

Furthermore, if desired, device 100 can be provided with just one electrostatic concentrator, rather than a plurality of electrostatic concentrators. In this construction, with the electric field along the X axis turned off and with the electric field along the Z axis turned on so as to initiate species separation using ion mobility separation, the analyzer can be stepped to any point along the Z axis, and then the electric field can be established along the X axis so as to concentrate a particular species at the high voltage electrode. Then a full spectral scan can be taken for analysis of that species. The process can be repeated to cover the full length of the Z axis.

Combinations of Spectroscopic Techniques

The present invention can also be utilized with spectroscopic techniques which combine several different spectroscopic approaches to achieve higher selectivity than is possible with only one spectroscopic technique. For example, combining Raman spectroscopy with UV fluorescence spectroscopy can be quite effective. Biological materials typically have UV absorption in the range of 230 nm to 300 nm and biological materials typically fluoresce in the range between 300 nm to visible light. This is not the case for most inorganic materials. Thus, UV fluorescence can be used to narrow down the range of potential materials which Raman spectroscopy or FTIR spectroscopy can then look for.

Spectroscopic Analysis Along the Z Direction

With device 100 shown in FIGS. 4 and 5, the different species are separated along the Z axis using ion mobility separation, and then the separated species are concentrated and then subjected to spectroscopic analysis.

Figure 6:
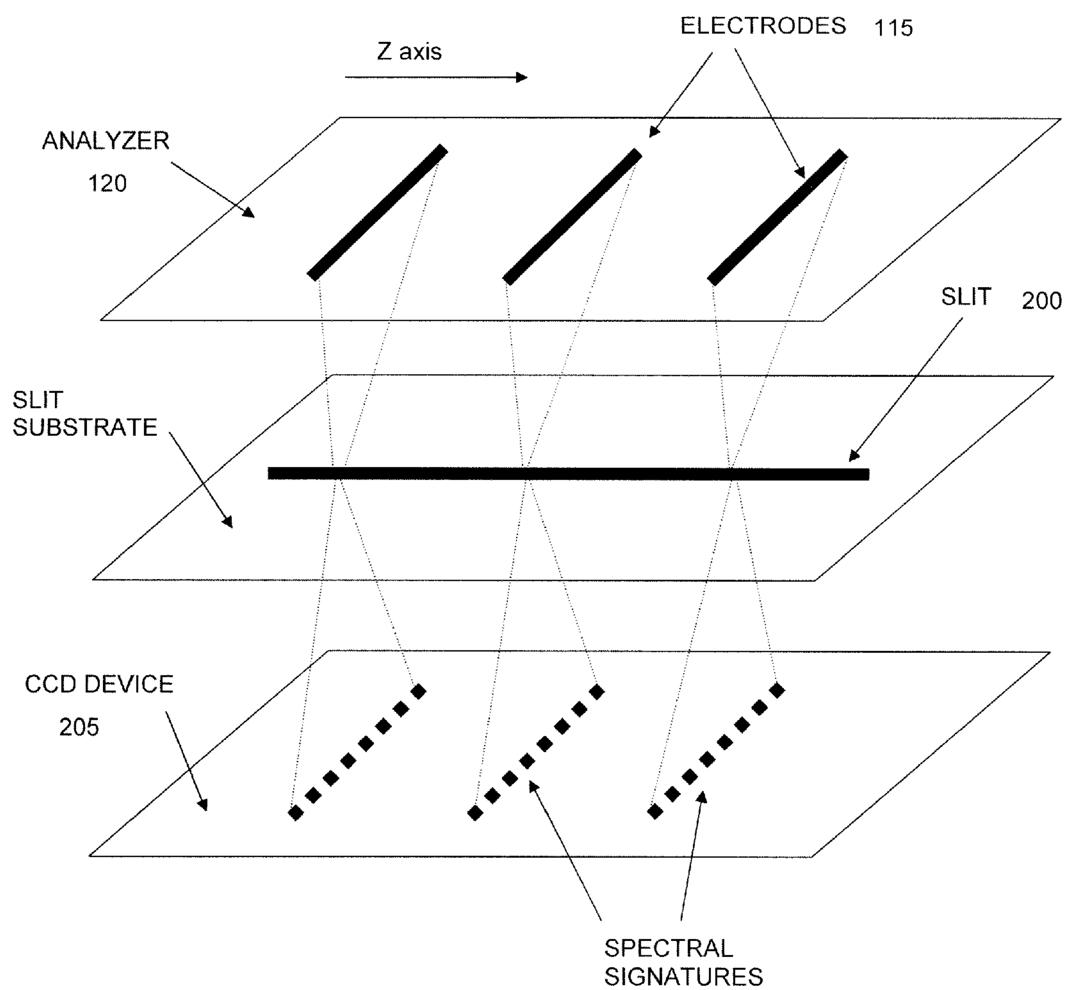
FIG. 6 is a schematic diagram showing spectroscopic analysis using a spectrometer slit and a 2-dimensional optical sensor disposed adjacent to the spectrometer slit.

In an additional form of the invention, spectroscopic analysis of the material along the Z axis on the analyzer substrate can be done using two dimensional charge-coupled device (CCD) sensors or other sensors. For example, and looking now at FIG. 6, the images of the samples separated along the Z axis of analyzer 120 can be focused onto a slit 200 of a spectrometer, where slit 200 is disposed along the Z axis. This construction causes each of the various input images entering the slit at various locations along slit 200 to be dispersed onto a two-dimensional sensor 205, with each of the slit-dispersed images being spaced along the Z axis of two-dimensional sensor. The two-dimensional sensor 205 can then be used to analyze the spectrum at any point along the Z axis of the analyzer, with each point being analyzed in parallel.

FURTHER MODIFICATIONS

It will be understood that many changes, in the details, materials, steps and arrangements of elements, which have been herein described and illustrated in order to explain the nature of the invention, may be made by those skilled in the art without departing from the scope of the present invention.

What is claimed is:

1. An apparatus for reliably and accurately detecting and identifying airborne particles, comprising:

an electrostatic concentrator operable to concentrate airborne particles about a site, the electrostatic concentrator comprising a ground electrode and a conductive high voltage electrode arranged to generate an electrical field having a large gradient in a small area, such that the airborne particles are guided toward the site; and a spectrometer operable to identify the airborne particles concentrated about the site.

2. The apparatus according to claim 1 wherein the ground electrode comprises a semitransparent ground electrode.

3. The apparatus according to claim 2 wherein the spectrometer comprises a light source and a light detector, and further wherein the light from the light source is focused on the site through the semitransparent ground electrode.

4. The apparatus according to claim 3 wherein the light source comprises a laser.

5. The apparatus according to claim 1 wherein the spectrometer comprises at least one from the group selected from a Raman spectrometer, an IR spectrometer, a UV spectrometer, an XRF spectrometer, an LIF spectrometer and a LIBS spectrometer.

6. The apparatus according to claim 1 wherein the spectrometer comprises at least two from the group selected from a Raman spectrometer, an IR spectrometer, a UV spectrometer, an XRF spectrometer, an LIF spectrometer and a LIBS spectrometer.

7. The apparatus according to claim 1 wherein the ground electrode comprises a ground electrode having an opening formed therein.

8. The apparatus according to claim 7 wherein the spectrometer comprises a light source and a light detector, and further wherein the light from the light source is focused on the site through the opening formed in the ground electrode.

9. The apparatus according to claim 8 wherein the light source comprises a laser.

10. The apparatus according to claim 7 wherein the spectrometer comprises at least one from the group selected from a Raman spectrometer, an IR spectrometer, a UV spectrometer, an XRF spectrometer, an LIF spectrometer and a LIBS spectrometer.

11. The apparatus according to claim 7 wherein the spectrometer comprises at least two from the group selected from a Raman spectrometer, an IR spectrometer, a UV spectrometer, an XRF spectrometer, an LIE spectrometer and a LIBS spectrometer.

12. The apparatus according to claim 1 wherein the apparatus has a transparent region adjacent to the conductive high voltage electrode.

13. The apparatus according to claim 12 wherein the spectrometer comprises a light source and a light detector, and further wherein the light from the light source is focused on the site through the transparent region adjacent to the conductive high voltage electrode.

14. The apparatus according to claim 13 wherein the light source comprises a laser.

15. The apparatus according to claim 12 wherein the spectrometer comprises at least one from the group selected from a Raman spectrometer, an IR spectrometer, a UV spectrometer, an XRF spectrometer, an LIF spectrometer and a LIBS spectrometer.

16. The apparatus according to claim 12 wherein the spectrometer comprises at least two from the group selected from a Raman spectrometer, an IR spectrometer, a UV spectrometer, an XRF spectrometer, an LIF spectrometer and a LIBS spectrometer.

17. The apparatus according to claim 12 wherein the conductive high voltage electrode is formed out of a semi-transparent material.

18. The apparatus according to claim 12 wherein the transparent region is formed out of a material having a low Raman cross-section material.

19. A method for reliably and accurately detecting and identifying airborne particles, comprising:

generating an electrical field having a large gradient in a small area using a ground electrode and a conductive high voltage electrode of an electrostatic concentrator;

passing the airborne particles across the electrostatic concentrator while operating the electrostatic concentrator so as to concentrate the airborne particles about a site; and operating a spectrometer so as to identify the airborne particles concentrated about the site.

20. The method according to claim 19 wherein operating the spectrometer comprises operating at least one from the group selected from a Raman spectrometer, an IR spectrometer, a UV spectrometer, an XRF spectrometer, an LIF spectrometer and a LIBS spectrometer.

21. The method according to claim 19 wherein operating the spectrometer comprises operating at least two from the group selected from a Raman spectrometer, an IR spectrometer, a UV spectrometer, an XRF spectrometer, an LIF spectrometer and a LIBS spectrometer.

* * * * *